United States Patent [19]

Desmons et al.

[11] Patent Number: 4,761,380
[45] Date of Patent: Aug. 2, 1988

[54] FERMENTATION CELL FOR CONTINUOUS OPERATION

[75] Inventors: Pierre Desmons, Nivelles; Philippe Mullier, Reves, both of Belgium

[73] Assignee: Abay S.A., Brussels, Belgium

[21] Appl. No.: 893,279

[22] Filed: Aug. 5, 1986

[30] Foreign Application Priority Data

Aug. 5, 1985 [EP] European Pat. Off. ........ 85201267.3

[51] Int. Cl.$^4$ .............................................. C12M 1/04
[52] U.S. Cl. .................................... 435/313; 435/288; 435/316; 435/813
[58] Field of Search ............... 435/299, 813, 288, 313, 435/316, 812, 819

[56] References Cited

U.S. PATENT DOCUMENTS

| | | | |
|---|---|---|---|
| 3,664,927 | 5/1972 | Shimizu et al. | 435/813 X |
| 3,880,716 | 4/1975 | Engelbart et al. | 435/813 X |
| 4,100,023 | 7/1978 | McDonald | 435/813 X |
| 4,302,546 | 11/1981 | Schlichting, Jr. | 435/316 X |
| 4,378,434 | 3/1983 | Prentice et al. | 435/813 X |
| 4,433,055 | 2/1984 | Kany | 435/819 X |

*Primary Examiner*—Larry Jones
*Attorney, Agent, or Firm*—Foley & Lardner, Schwartz, Jeffery, Schwaab, Mack, Blumenthal & Evans

[57] ABSTRACT

A fermenter cell disposed so that the primary axis of the cell is approximately horizontal comprises solid partitions, arranged perpendicularly to the primary axis, which separate the cell into several chambers. The partitions are provided with apertures, each at a predetermined height, which allow liquid to pass; in addition, gas evacuation pipes are provided in the upper part of the chambers.

12 Claims, 1 Drawing Sheet

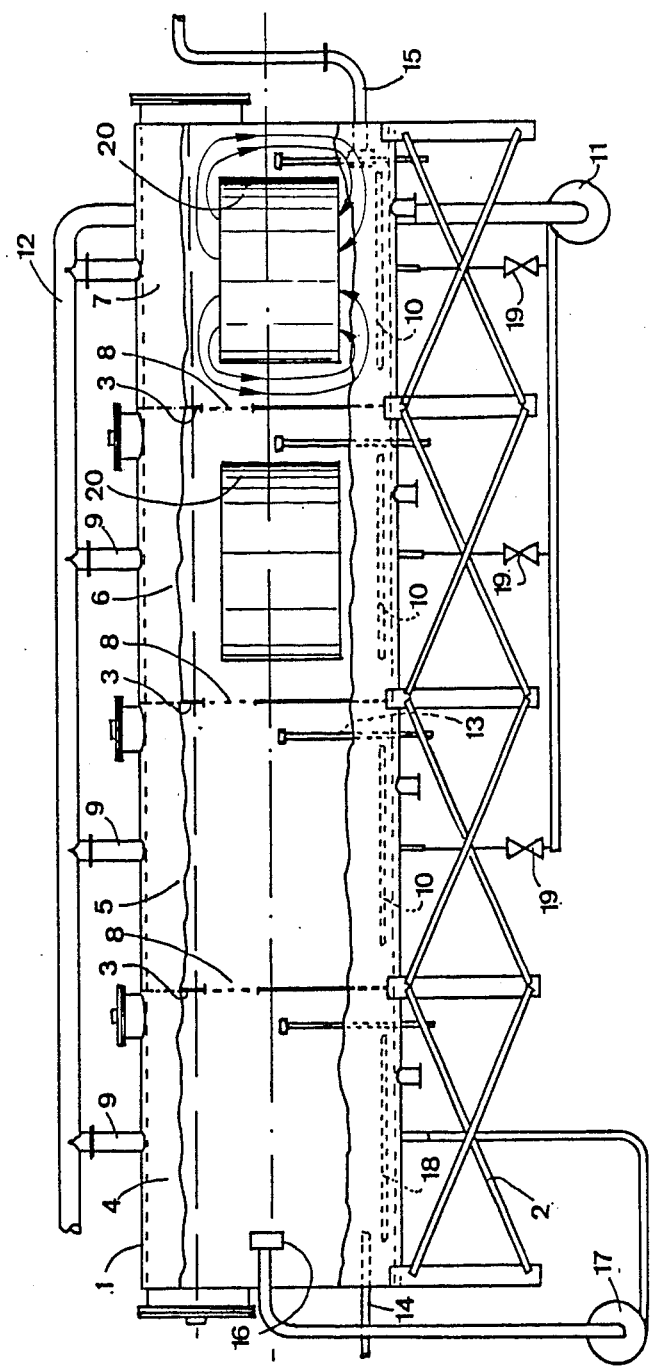

FERMENTATION CELL FOR CONTINUOUS OPERATION

BACKGROUND OF THE INVENTION

1. Field of the Invention

The present invention relates to a fermentation cell in which a liquid is subjected to the action of microorganisms that are fixed on solid supports or that form freely moving cell masses, via agglomeration or flocculation, of a sufficiently large size to be retained by appropriately positioned grids or lattices. The solid supports either can have limited movement, as in the case of plastic bands fixed on a grid, or can be free moving, like granules or small balls of a material having a density greater than the density of the liquid. The solid supports can also take the form of balls of an appropriate gel, for example, alginates, acrylamides, etc. In the fermenter, the liquid circulates continuously from an inlet pipe positioned at one end of the fermenter toward an outlet pipe at the other end.

2. Related Art

The principles by which fermenters as described above operate are known. The typical fermenter of this type comprises, for example, a cylindrical cell having a primary axis that is vertical, the inlet pipe being disposed, as the case may be, either at the bottom or at the top of the cell, and the outlet pipe at the opposite end of the cell.

In these known fermenters, the microorganism supports, having a density greater than the liquid, are often carried upward because of gas absorbed, adsorbed or otherwise captured on the surface, or entrapped in the pores, of the supports, to form bridge structures. This grouping together of the supports results in a decrease in the support-surface area that is readily accessible to the liquid in the fermenter, preventing the fermenter from functioning normally. The deleterious effects from the formation of bridge structures can be reduced if the cell is separated by means of horizontal lattices into several adjacent chambers. But even by this approach, the packing of the supports against the lattices may seriously disturb effective operation of the fermenter.

SUMMARY OF THE INVENTION

It is therefore an object of the present invention to avoid these inconveniences, thereby making the fermentation more efficient, and to provide a greater yield from the fermenter installation, as compared to the yield of a conventional installation with the same fermenter volume.

To achieve this object, the fermenter according to the present invention comprises a cell having a primary axis that is disposed approximately horizontally; moreover, the cell is separated into several chambers by means of partitions perpendicular to the primary axis of the cell. The walls are provided with apertures which allow the liquid to pass in a horizontal direction. The apertures are disposed at specific, predetermined heights, and the upper part of the chambers defined by the partitions are provided with gas evacuation pipes.

BRIEF DESCRIPTION OF THE DRAWINGS

The present invention is described by reference to the following example and the related drawing, which presents a schematic cross-sectional view of a fermenter according to the present invention.

DETAILED DESCRIPTION OF THE PREFERRED EMBODIMENTS

In the FIGURE, a cell 1 is supported by a framework 2 in such a manner that the primary axis of the cell extends in a horizontal direction. The cross section of the cell can be square, but preferably is circular. The diameter of the cell is selected as a function of the particular fermentation under consideration. In the case of a transforming fermentation, e.g., in which molasses is transformed into ethanol, a diameter between about 1 and 5 meters is suitable.

Cell 1 is separated by partitions 3 into several chambers 4, 5, 6 and 7, each having a length that is preferably about equal to the diameter of the cell. But very good results are generally obtained when the length of these chambers is between about one-half and two times the diameter of the cell. In any event, these limitations need not be considered as restrictive. The different chambers can even have unequal lengths.

Each of the partitions 3 comprises a window or aperture positioned at a height corresponding approximately to the level of the liquid in the cell. This level is preferably maintained between about 0.6D and 0.8D, D being the diameter of the cell. When the microorganism supports have only limited movement (for example, when the supports are in the form of thin plates, of a density lower than the density of the liquid, having one end fixed to the base of the chamber), the apertures are kept open. In the case where the masses or supports of microorganisms are free moving, as is true for small balls of alginate gel having a density greater than that of the liquid, the apertures 8 preferably support lattices comprised of a material, such as stainless steel, that is inert with respect to the liquid to be treated, to the microorganism supports and to the microorganisms themselves, whether fixed or not. The term "lattice" is used here to designate any structure that allows the liquid to pass while preventing the passage of the masses or supports of microorganisms, for example, by virtue of the choice of mesh size for the lattice. Instead of being positioned at the height of the level of the liquid, the apertures 8 can be disposed at a much lower level, preferably at a place where the microorganism supports move parallel to the partitions 3 without tending to collect against the lattice and clog the openings.

An evacuation pipe 9 for gases is located at the upper part of each chamber, while a gas injector 10 is provided at the base of chambers 5, 6, 7. The injectors 10 are connected to the outlet of a compressor 11, the inlet of which is connected to a conduit 12 into which pipes 9 empty. Probe 13 for obtaining samples of the liquid in the cell can be disposed in each chamber. An input pipe 14 brings the liquid to be treated into chamber 4. The liquid then passes through the apertures 8 from chamber to chamber, and finally exits chamber 7 by an outlet pipe 15. The liquid level within chambers 4, 5, 6, 7 is maintained, respectively, at a desirable height, for example, by the appropriate disposition of the outlet pipe. (A gooseneck configuration for the outlet pipe is shown in the FIGURE.)

If, for example, fermentation is very active in the first chamber 4, possibly causing appearance of foam, a gas injector need not be provided at the bottom of chamber 4. But if a mixing effect is desirable in the first chamber, it is preferable to produce this effect by means of a liquid injection, eventually with the addition of an antifoaming agent. By this approach, the feed liquid can be injected under a selected pressure and in a desired direction, for example, by an appropriate disposition of the inlet pipe, not shown, to bring about agitation and mixing of the feed liquid.

According to another variation of the present invention, as shown in the FIGURE, a sample of the liquid is taken at an orifice 16 connected to a pump 17. The outlet of the feed pump leads to an injection pipe 18 at the bottom of chamber 4. It is possible, and sometimes desirable, for the second chamber 5 also to be provided with a liquid injector which can be fed by the same pump 17.

The removal of the liquid can be carried out across a lattice that retains the supports or masses of microorganisms and allows only the liquid to pass. Alternatively, removal of the liquid can also include the removal of the microorganism supports, which are then reinjected simultaneously with the liquid.

The effective volume of the microorganism (i.e., the total volume of all support structures) in each chamber can differ from chamber to chamber, and the nature of the supports and of the microorganisms on each type of support can also differ between chambers. In particular, the microorganisms in each chamber can be chosen as a function of the conditions of reproduction and favorable longevity that arise from the composition of the liquid chosen for each of the chambers. As the conditions in the different chambers generally do not vary to a significant degree, however, it is possible and simpler to maintain all of the chambers in an identical manner.

It must be emphasized that the fermenter cell of the present invention is separated into quasi-independent chambers. The entire cell is not a perfectly mixed fermenter, but rather comprises different fermenters in adjacent chambers. This is also true if the same supports for the same microorganisms are used in the same concentrations in all of the chambers.

In each chamber, appropriate measures can be taken to assure a convenient mixing or to effect optimum biological reaction yield. Thus, if the biological reaction is favored by a small quantity of air or other gaseous adjuvant, the compressor 1 can provide a controllable input of air or the gaseous adjuvant, which is then mixed in small proportion with the gas collected by the pipes 9 and sent into the different chambers in predetermined quantities, for example, in a relatively small quantity in chamber 5 and in increasing quantities in the following chambers where the fermentation activity is increasingly weaker. The control of these quantities is accomplished, for example, by means of values 19 or by other appropriate accessories, which in turn are controlled by a central, computer-directed controller, so that the system functions in accord with conveniently selected parameters and measured sizes.

When the liquid is molasses in aqueous solution and the microorganisms are yeast, for example, a Saccharomyces species, or bacteria, like a Zymomonas species, the sugar concentration of liquid at the inlet can be very large, greater than 15%, for example. At outlet 15, this concentration may fall to a value of less than 1% if the residence time of the liquid in the fermenter reaches at least 4 hours. During fermentation, up to 95% of the sugar is transformed into ethanol and carbonic acid anhydride. The production of ethanol can also reach the range of 25 kg per hour and per cubic meter of influent.

In large-size fermenters, it is particularly advantageous to take measures to assure a thorough mixture between liquid and microorganism masses or supports. Such measures include, for example, placing in opposing disposition the injectors 10 or 18 and means, such as a central pipe 20, for separating the opposing zones of fluid movement in the chambers, for example, the respective zones of rising and descending movement of liquid.

When the fermentation is very intense, the natural cooling across the partitions of the cell may be insufficient. In this case, means for cooling the liquid must be provided. For cells of relatively small capacity, a cooled enclosure for the cell, such as a double wall, may suffice. For greater capacities, it is possible to position a network of cooling tubes in an appropriate place in each chamber, as the needs for intense cooling dictate. The coolig tubes can, in particular, be located in a space surrounding pipe 20. It is also possible to cool all of the chambers by means of upright pipes traversing the cell from chamber to chamber. The pipes may be disposed, for example, above or below the pipes 20 or placed along the cylindrical wall of cell 1 at such distances that they preferably (but not necessarily) do not cross the pipes 20. Alternatively, the pipes 20 can be fixed to these cooling tubes in order to take advantage of the good heat conductivity of the material from which the pipes 20 are fabricated.

What is claimed is:

1. Fermentation apparatus for subjecting a liquid to the action of microorganisms that form cell masses or are fixed on solid supports in said apparatus, wherein said liquid is circulated continuously from an inlet pipe towards an outlet pipe, comprising (1) a closed cell having an approximately horizontal primary axis, said cell being divided into a plurality of chambers by solid partitions positioned vertically at predetermined intervals in said cell, wherein at least some of said partitions are each provided at a predetermined height with an aperture allowing liquid to pass through the partition; and (2) evacuation means for evacuating gas of said chambers.

2. Apparatus according to claim 1, wherein a lattice is provided in one or more of the apertures.

3. Apparatus according to claim 1, further comprising injector means for injecting a gas or liquid into at least one of said chambers.

4. Apparatus according to claim 3, wherein said evacuation means comprises compressor means for collecting gas from said chambers, said gas being reinjected into at least one of said chambers. by said injector means.

5. Apparatus according to claim 4, wherein said compressor means provides a controllable input to said chambers of a gaseous adjuvant favoring fermentation.

6. Apparatus according to claim 3, wherein said injector means comprises pump means for recirculating through said cell liquid previously removed from said chambers.

7. Apparatus according to claim 1, further comprising at least one probe means for obtaining a sample of said liquid in at least one of said chambers.

8. Apparatus according to claim 1, wherein said microorganisms are fixed on solid supports that has an effective volume representing more than one-third the volume of liquid in each of said chambers.

9. Apparatus according to claim 1, further consisting essentially of cooling means for cooling said liquid.

10. Apparatus according to claim 1, wherein at least one chamber of said plurality contains an open pipe positioned vertically, said pipe defining a movement of said liquid in one direction inside and in another direction outside of the pipe.

11. Apparatus according to claim 1, wherein said cell accommodates a level of said liquid in said chamber that is between about 0.6D and 0.8D in height, D being the diameter of said cell.

12. Fermentation apparatus for subjecting a liquid to the action of microorganisms that form cell masses or are fixed on solid supports in said apparatus, wherein said liquid is circulated continuously from an inlet pipe towards an outlet pipe, comprising (1) a cell having an approximately horizontal primary axis, said cell being divided into a plurality of chambers by solid partitions positioned vertically at predetermined intervals in said cell, wherein said partitions are each provided at a predetermined height with an aperture allowing liquid to pass through the partition, each of the apertures being provided below the level of said liquid in said cell; and (2) evacuation means for evacuating gas of said chambers.

* * * * *